US00PP25474P3

(12) United States Plant Patent
Dirr

(10) Patent No.: US PP25,474 P3
(45) Date of Patent: Apr. 28, 2015

(54) ***LANTANA* PLANT NAMED 'PIIL-SSUS'**

(50) Latin Name: *Lantana camara*
Varietal Denomination: PIIL-SSUS

(71) Applicant: Matthew A. Dirr, Watkinsville, GA (US)

(72) Inventor: Matthew A. Dirr, Watkinsville, GA (US)

(73) Assignees: Plant Introductions, Inc., Watkinsville, GA (US); University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 13/694,991

(22) Filed: Jan. 23, 2013

(65) Prior Publication Data

US 2014/0208473 P1 Jul. 24, 2014

(51) Int. Cl.
*A01H 5/00* (2006.01)

(52) U.S. Cl.
USPC ..... Plt./227

(58) Field of Classification Search
USPC ..... Plt./227
See application file for complete search history.

(56) References Cited

U.S. PATENT DOCUMENTS

| | | | |
|---|---|---|---|
| PP19,548 | P2 | 12/2008 | Dirr |
| PP21,539 | P3 | 11/2010 | Griffith |
| 2012/0084892 | P1 | 4/2012 | Kardos |

*Primary Examiner* — Kent L Bell
(74) *Attorney, Agent, or Firm* — Lathrop & Gage LLP

(57) ABSTRACT

A new and distinct cultivar of *Lantana* plant named 'PIIL-SSUS', characterized by its low growing, layered and spreading growth habit; leathery, scabrous dark green foliage; continuous flowering; and bright golden yellow flower buds that open to bright golden yellow and age to pale yellow and eventually to white. There are no other cultivars of *Lantana* with this combination of characteristics known to the inventor.

2 Drawing Sheets

Genus and species of plant claimed: *Lantana camara.*
Variety denomination: 'PIIL-SSUS'.

BACKGROUND OF THE INVENTION

The present invention relates to a new and distinct cultivar of *Lantana* plant, botanically known as *Lantana camara*, and hereinafter referred to by the cultivar name 'PIIL-SSUS'.

The new *Lantana* plant originated as a naturally occurring, non-induced branch mutation on a plant of *Lantana camara* 'Sunny Side Up' (U.S. Plant Pat. No. 23,650). The cultivar 'PIIL-SSUS' originated and was discovered in a cultivated environment in a garden in Watkinsville, Ga.

Asexual reproduction of the new cultivar by stem cuttings in Watkinsville, Ga. has shown that all the unique features of this new *Lantana*, as herein described, are stable and reproduced true-to-type through successive generations of such asexual propagation.

SUMMARY OF THE INVENTION

Plants of the new cultivar 'PIIL-SSUS' have not been observed under all possible environmental conditions. The phenotype may vary somewhat with changes in light, temperature, soil and rainfall without, however, any variance in genotype.

The following traits have been repeatedly observed and are determined to be unique characteristics of 'PIIL-SSUS'. These characteristics in combination distinguish 'PIIL-SSUS' as a new and distinct cultivar:

1. Low growing, layered and spreading growth habit;
2. Leathery, scabrous dark green foliage;

3. Continuous flowering; and
4. Bright golden yellow flower buds that open to bright golden yellow and age to pale yellow and eventually to white.

There are no other cultivars of *Lantana* with this combination of characteristics known to the inventor.

Plants of the new *Lantana* 'PIIL-SSUS' differ from plants of the parent, 'Sunny Side Up', primarily in flower color, as plants of 'Sunny Side Up' have yellow flower buds that open to yellow with a darker golden-yellow center and age to white with a yellow center, whereas plants of 'PIIL-SSUS' have bright golden yellow flower buds that open to bright golden yellow and age to pale yellow and eventually to white.

Plants of the new *Lantana* 'PIIL-SSUS' can be compared to plants of *Lantana* 'PIIL-SSUS'. However, in side-by-side comparisons conducted in Watkinsville, Ga., plants of 'PIIL-SSUS' differed from plants of 'PIIL-CHW' (U.S. Plant patent application Ser. No. 13/694,989) primarily in flower color, as plants of 'PIIL-SSUS' have bright golden yellow flower buds that open to bright golden yellow and age to pale yellow and eventually to white, whereas plants of 'PIIL-CHW' have pale yellow flower buds that open to medium yellow with a darker yellow-orange center and age to white with a medium yellow center.

Plants of the new *Lantana* 'PIIL-SSUS' can be compared to plants of *Lantana* 'LCBCW' (not patented). However, in side-by-side comparisons conducted in Watkinsville, Ga., plants of 'PIIL-SSUS' differed from plants of 'LCBCW' in the following ways. Plants of 'PIIL-SSUS' had darker green, thicker, more scabrous foliage than plants of 'LCBCW'. Plants of 'PIIL-SSUS' had brighter flower color and larger flowers than plants of 'LCBCW'. Plants of 'PIIL-SSUS' had an overall larger growth habit than plants of 'LCBCW'.

BRIEF DESCRIPTION OF THE DRAWINGS

The accompanying color photographs illustrate the flower and foliage characteristics and the overall appearance of the new *Lantana*, showing the colors as true as it is reasonably possible to obtain in color reproductions of this type. Colors in the photographs may differ slightly from the color values cited in the detailed botanical description which accurately describe the colors of the new *Lantana*.

DETAILED DESCRIPTION

Figure 1:
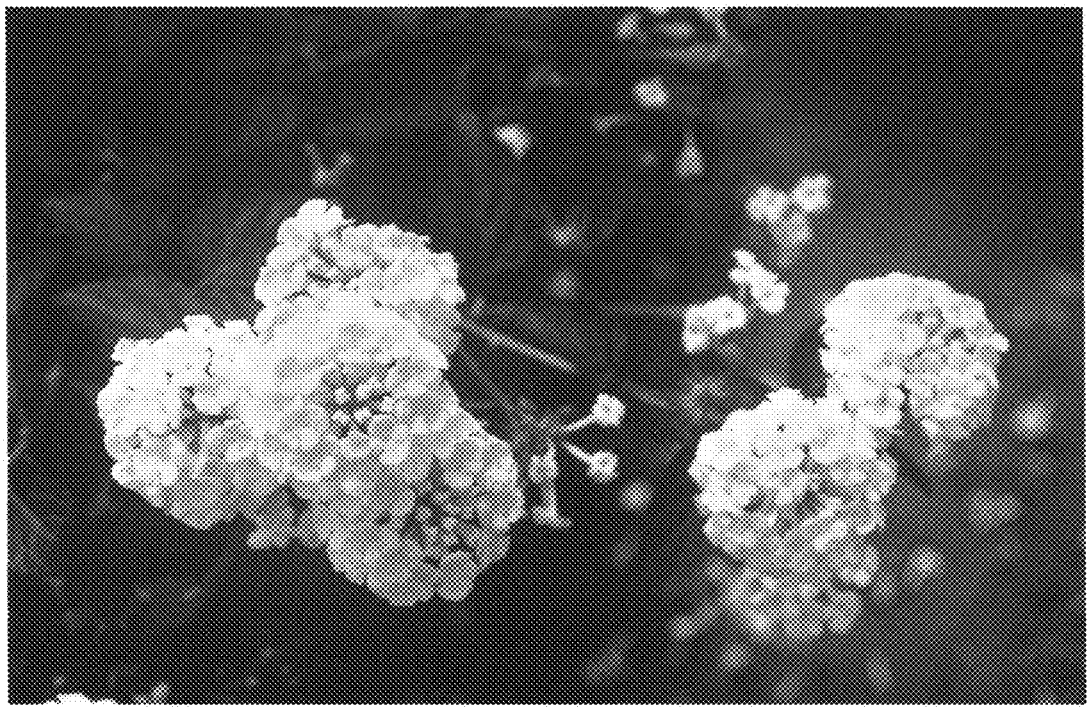
FIG. 1 illustrates a close-up view of the inflorescences and foliage of 'PIIL-SSUS'.
Figure 2:
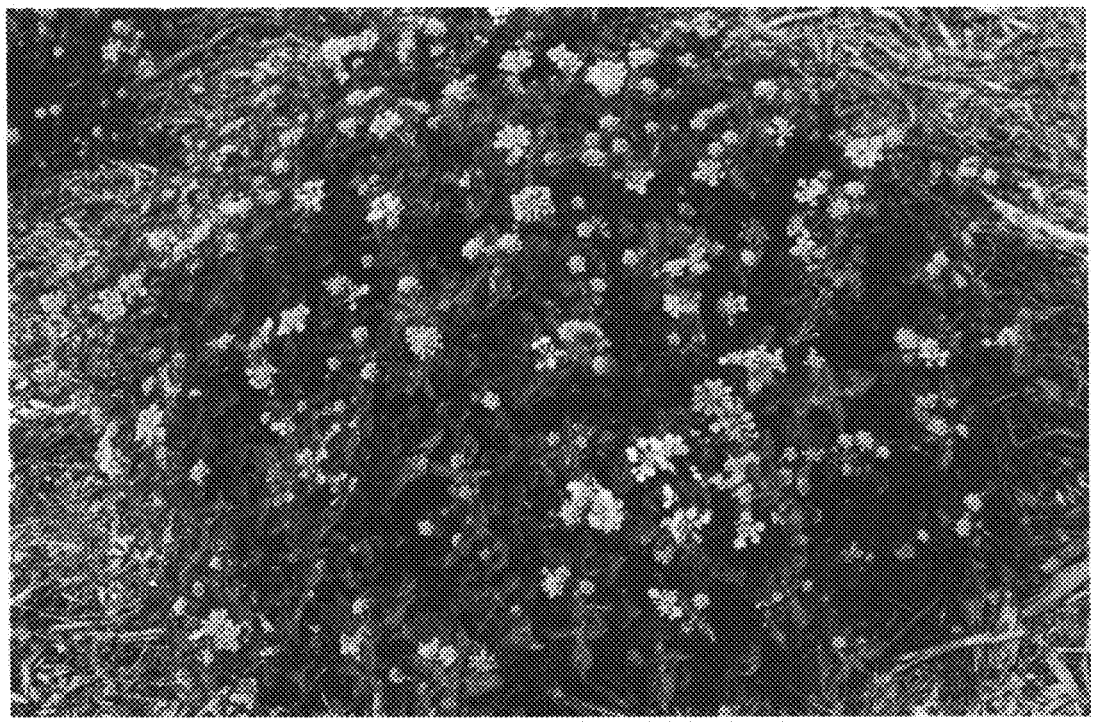
FIG. 2 illustrates the overall appearance of a mature plant of 'PIIL-SSUS' planted in the ground.

In the following description, color references are made to The Royal Horticultural Society Colour Chart, 2007 Edition, except where general terms of ordinary dictionary significance are used. Plants used for the description were approximately six months old and were grown in 11.8 L containers in full sun under outdoor conditions in a nursery in Watkinsville, Ga.

Botanical classification: *Lantana camara* 'PIIL-SSUS'.

Parentage: *Lantana camara* 'Sunny Side Up' (U.S. Plant Pat. No. 23,650).

Propagation: Stem cuttings.

Time to initiate roots, summer: About 10 days at 32° C.

Plant description: Herbaceous flowering plant, subshrub, low growing, layered and spreading growth habit. Freely branching habit with about three to four primary lateral branches per plant; each primary lateral branch with potentially two secondary lateral branches developing at each node. Pinching enhances lateral branch development. Length about 71 cm in height.

- *Root description*.—Numerous, fine, fibrous and well-branched.
- *Plant size*.—About 71 cm in height from the soil level to the top of the inflorescences, and about 137 cm in diameter. Young stems having a diameter of about 3 mm and a squarish shape. Mature stems having a diameter of about 4 mm or more and a rounded shape. Quantity of main branches per plant 3-4. Length of stems about 71 cm.
- *Stem strength*.—Strong, but flexible.
- *Stem texture*.—Coarse, pubescent.
- *Stem color* (*young*).—144A. Color (mature): 199A.
- *Internode length*.—About 3.4 cm.

Vegetative buds: Opposite in arrangement, valvate, ovoid, pubescent.

- *Color*.—144A.
- *Size*.—About 1 mm in length and about 1 mm in width.

Foliage description:

- *Arrangement*.—Opposite, simple.
- *Length*.—About 4.2 cm.
- *Width*.—About 2.8 cm.
- *Shape*.—Ovate.
- *Apex*.—Acute.
- *Base*.—Cuneate.
- *Margin*.—Crenate.
- *Texture* (*upper surface*).—Leathery, moderately waxy, with scabrous pubescence.
- *Texture* (*lower surface*).—Rough, with hispid pubescence.
- *Venation pattern*.—Pinnate.
- *Venation color* (*upper surface*).—144A.
- *Venation color* (*lower surface*).—144A.
- *Fragrance*.—Pungent, mint-like.
- *Color of developing foliage* (*upper surface*).—146B.
- *Color of developing foliage* (*lower surface*).—147B.
- *Color of mature foliage* (*upper surface*).—147A.
- *Color of mature* (*lower surface*).—147B.
- *Petiole length*.—About 9 mm.
- *Petiole diameter*.—About 2 mm.
- *Petiole texture, both surfaces*.—Hispid pubescence.
- *Petiole color* (*upper and lower surfaces*).—144A.

Flower description:

- *Flower type and habit*.—Small salverform flowers arranged in axillary corymbs; flowers face mostly upward or outward. Flowers are self-cleaning. Freely flowering with potentially two inflorescences per node; typically about 22 to 28 flowers per corymb.
- *Natural flowering season*.—Spring until the first frost in fall; flowering is continuous.
- *Flower longevity on the plant*.—About one week.
- *Fragrance*.—None observed.
- *Inflorescence diameter*.—About 4 cm.
- *Inflorescence height*.—About 2.5 cm.
- *Flower bud length*.—About 1 cm.
- *Flower bud diameter*.—About 3 mm.
- *Flower bud shape*.—Oblong.
- *Flower bud color*.—17C.
- *Flower appearance*.—Flared trumpet, corolla fused, four-parted; flowers roughly rectangular in shape.
- *Diameter*.—About 1 cm.
- *Corolla tube length*.—About 1 cm.
- *Depth* (*height*).—About 1.5 cm.
- *Throat diameter*.—About 1.5 mm.
- *Pedicels*.—None observed, flowers not stalked.

Petals:

- *Arrangement/appearance*.—Single whorl of four petals, fused into flared trumpet.
- *Diameter*.—About 9 mm by 11 mm.
- *Depth* (*height*).—About 1.5 cm.
- *Throat diameter*.—About 1 mm.
- *Tube length*.—About 1.1 cm.
- *Petal length from throat*.—About 5 mm for the upper petal, about 4 mm for the lower petal, and about 4 mm for the lateral petals.
- *Petal width*.—About 6 mm for the upper petal, about 5 mm for the lower petal, and about 4 mm for the lateral petals.
- *Petal shape*.—Spatulate to somewhat orbicular.
- *Petal apex*.—Obtuse.
- *Petal base*.—Fused.
- *Petal margin*.—Entire.
- *Petal texture, upper and lower surfaces*.—Smooth, glabrous.
- *Petal color* (*young*).—Upper surface: 17C and lower surface: 14C. Color of throat: 17C. Color of corolla tube: 12C.
- *Petal color* (*mature*).—Upper and lower surfaces, throat, and corolla tube: 10C. Petal color (aged): upper and lower surfaces, throat, and corolla tube: 157D.

Sepals:

*Arrangement/appearance*.—One sepal per flower at the base of the corolla, leaf-like. Length is about 6 mm. Width is about 2 mm.

*Shape*.—Lanceolate.

*Apex*.—Acute.

*Margin*.—Entire.

*Texture, upper and lower surface*.—Scabrous.

*Sepal color, upper and lower surfaces*.—146A.

Peduncles:

*Length*.—About 3.5 cm.

*Diameter*.—About 1.5 mm.

*Angle*.—About 45 degrees from the stem.

*Strength*.—Flexible, but strong.

*Color*.—144A.

Stamens:

*Quantity/arrangement*.—Four per flower, adnate to the inside of the corolla tube.

*Anther shape*.—Oblong.

*Anther length*.—1 mm.

*Anther width*.—Less than 1 mm.

*Anther color*.—13B.

*Pollen amount*.—Produced in very small quantities, and 13B in color.

Pistils:

*Quantity*.—One inferior pistil per flower.

*Pistil length*.—About 3.5 mm.

*Stigma shape*.—Rounded.

*Stigma size*.—About 1 mm in diameter.

*Stigma color*.—145B.

*Style length*.—About 1.5 mm.

*Style color*.—145B.

*Ovary size*.—About 1 mm in diameter.

*Ovary color*.—145A.

Fruit:

*Type/appearance*.—Drupe.

*Shape*.—Round.

*Diameter*.—About 5 mm.

*Mature color*.—202A.

*Number per infructescence*.—Ranges from zero to about five.

Disease/pest resistance: Plants of the claimed *Lantana* cultivar grown in the garden have not been noted to be susceptible or resistant to pathogens and pests common to *Lantana*.

I claim:

1. A new and distinct *Lantana* plant named 'PIIL-SSUS', as illustrated and described herein.

* * * * *